(12) United States Patent
Peck et al.

(10) Patent No.: US 9,095,324 B2
(45) Date of Patent: *Aug. 4, 2015

(54) PACKAGE ASSEMBLY

(75) Inventors: James M. Peck, Maple Grove, MN (US); Ben Prusi, Maple Grove, MN (US); Diona Sommario, Eden Prairie, MN (US); Kim Robertson, Forest Lake, MN (US); Samir Shrestha, New Brighton, MN (US); Tom Arthur, Champlin, MN (US); Tony Suardini, Rogers, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1227 days.

This patent is subject to a terminal disclaimer.

(21) Appl. No.: 12/143,164

(22) Filed: Jun. 20, 2008

(65) Prior Publication Data

US 2009/0314676 A1 Dec. 24, 2009

(51) Int. Cl.
| | |
|---|---|
| *A61B 17/06* | (2006.01) |
| *A61B 19/02* | (2006.01) |
| *A61L 2/20* | (2006.01) |
| *B65D 33/01* | (2006.01) |
| *A61F 2/00* | (2006.01) |
| *A61L 2/26* | (2006.01) |
| *A61M 25/00* | (2006.01) |
| *B65B 55/10* | (2006.01) |

(52) U.S. Cl.
CPC ............... *A61B 19/026* (2013.01); *A61L 2/206* (2013.01); *B65D 33/01* (2013.01); *A61B 2019/027* (2013.01); *A61B 2019/0268* (2013.01); *A61B 2019/0273* (2013.01); *A61B 2019/0285* (2013.01); *A61F 2/0095* (2013.01); *A61L 2/26* (2013.01); *A61L 2202/181* (2013.01); *A61M 25/002* (2013.01); *B65B 55/10* (2013.01)

(58) Field of Classification Search
CPC ........ A61F 2/0095; A61L 2/206; B65D 75/30
USPC ......... 206/438, 204, 205, 219, 220, 221, 222, 206/213.1
See application file for complete search history.

(56) References Cited

U.S. PATENT DOCUMENTS

| | | | | |
|---|---|---|---|---|
| 3,391,047 | A * | 7/1968 | Kopp | 156/553 |
| 3,754,700 | A * | 8/1973 | Bonk | 206/439 |
| 3,939,971 | A * | 2/1976 | Tulis | 206/205 |
| 3,942,634 | A * | 3/1976 | Gandi et al. | 206/210 |
| 4,660,721 | A * | 4/1987 | Mykleby | 206/439 |
| 4,714,595 | A * | 12/1987 | Anthony et al. | 422/294 |
| 4,730,726 | A | 3/1988 | Holzwarth | |
| 4,861,632 | A * | 8/1989 | Caggiano | 428/35.2 |

(Continued)

FOREIGN PATENT DOCUMENTS

| | | |
|---|---|---|
| WO | 9903754 | 1/1999 |
| WO | 2004071308 | 8/2004 |

*Primary Examiner* — Steven A. Reynolds
*Assistant Examiner* — King M Chu
(74) *Attorney, Agent, or Firm* — Seager, Tufte & Wickhem, LLC

(57) ABSTRACT

A method and apparatus for packaging a medical device includes a package assembly that defines a multi-chambered interior. The interior chambers include a primary and a secondary chamber. A partition, which has a gas permeable vent, separates the primary chamber from the secondary chamber. The package is constructed from a variety of materials that provide the interior with a long term, low humidity, sterile environment.

12 Claims, 7 Drawing Sheets

(56) References Cited

U.S. PATENT DOCUMENTS

| | | | |
|---|---|---|---|
| 4,941,308 A * | 7/1990 | Grabenkort et al. | 53/425 |
| 5,459,978 A * | 10/1995 | Weiss et al. | 53/425 |
| 5,577,368 A | 11/1996 | Hamilton et al. | |
| 5,690,623 A * | 11/1997 | Lenz et al. | 604/333 |
| 5,698,217 A * | 12/1997 | Wilking | 424/448 |
| 5,947,288 A * | 9/1999 | Dykstra et al. | 206/439 |
| 6,059,112 A * | 5/2000 | Dykstra et al. | 206/438 |
| 6,174,934 B1 | 1/2001 | Sun et al. | |
| 6,575,627 B2 * | 6/2003 | Huseman et al. | 383/38 |
| 6,594,971 B1 * | 7/2003 | Addy et al. | 53/413 |
| 7,000,770 B2 | 2/2006 | Clarke et al. | |
| 7,040,485 B2 | 5/2006 | Gupta et al. | |
| 7,178,555 B2 | 2/2007 | Engel et al. | |
| 7,261,205 B2 | 8/2007 | Cervantes | |
| 7,631,760 B2 * | 12/2009 | Guelzow et al. | 206/438 |
| 2003/0178329 A1 * | 9/2003 | Furukawa et al. | 206/213.1 |
| 2004/0050437 A1 * | 3/2004 | Engel et al. | 137/843 |
| 2004/0155053 A1 | 8/2004 | Sanchez | |
| 2004/0187438 A1 | 9/2004 | Clarke et al. | |
| 2004/0222116 A1 * | 11/2004 | Bauer | 206/438 |
| 2004/0243214 A1 | 12/2004 | Farrell et al. | |
| 2006/0016708 A1 | 1/2006 | Ingraham | |
| 2006/0186010 A1 * | 8/2006 | Warnack et al. | 206/438 |
| 2006/0260967 A1 * | 11/2006 | Clarke et al. | 206/438 |
| 2007/0084144 A1 | 4/2007 | Labrecque et al. | |
| 2007/0092167 A1 * | 4/2007 | Tilman et al. | 383/63 |
| 2011/0079525 A1 * | 4/2011 | Peck et al. | 206/438 |

* cited by examiner

PACKAGE ASSEMBLY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to a package assembly suitable for use with environmentally sensitive products, and more particularly for use with one or more medical devices.

2. Description of the Related Art

Packages suitable for use with environmentally sensitive products such as medical devices employ various configurations and/or mechanisms to provide the package interior, and the medical device contained therein, with a secure and sterile storage environment. Modern medical devices however, often employ a drug component that can complicate the packaging solution by requiring more than just a sterile environment.

From providing moisture control, to physical protection, the addition of a drug component, such as a coating, upon a medical device to be packaged requires more dynamic packaging solutions than those presently available.

Some examples of known packaging solutions that are directed to medical devices include:

U.S. Pat. No. 5,577,368 to Hamilton et al. and U.S. Pat. No. 6,174,934 to Sun et al. The packages and packaging procedures described in these references seek to remove the oxygen/atmosphere from the packaging prior to radiation sterilization of medical implants made of polymeric material in order to reduce the wear resistance of the polymeric implant.

U.S. Pat. No. 4,941,308 to Grabenkort et al. discloses sterilizing the interior of a package before placing the product in an inner package, sterilizing the product in the inner package, and then placing the inner package into an outer package. Grabenkort et al. uses ethylene oxide gas (EtO) for the sterilization.

U.S. Pat. No. 7,040,485 to Gupta and U.S. Publication 2007/0084144 A1 to Labrecque et al. describe pouches that employ gas permeable headers intended to allow transfer of gasses between the pouch interior and the header before and during sterilization. These headers extend out from the pouch and may be optionally removed.

Despite the availability of such packaging solutions, there remains a need for an efficient packaging assembly and method suitable for use with particularly specialized products such as medical devices, and particularly medical devices having a drug coating or similar therapeutic component.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a package assembly constructed from a gas impermeable shell or walls that define the package interior. The interior is divided into chambers by a partition. The partition defines a vent of at least one gas permeable material. In some embodiments the vent allows gas to flow only from a primary chamber (a product containment chamber) to an adjacent, secondary chamber (which may contain or include a desiccant or moisture absorbing substance).

The interior comprises two or more chambers as desired. The chambers of the assembly are separately accessible and can be individually sealed to allow one chamber (and/or its contents) to be manipulated without compromising the sterile environment of the adjacent chamber.

In some embodiments the outer shell of the assembly is characterized has having first (i.e., front) and second (i.e., back) walls. The walls may be of identical or significantly different construction, and may include a variety of materials and characteristics in their construction. For example, in some embodiments the package assembly comprises a UV barrier in the make-up of one wall while such a barrier may be considered an unnecessary expense on the opposing wall. Depending on the nature of the product to be contained in the assembly, the environment where it is to be stored, etc., embodiments of the invention will include walls having one or more layers of material to provide at least one oxygen barrier layer, at least one puncture resistant layer, at least one moisture vapor barrier layer, at least one ultraviolet barrier layer, and any combination thereof.

In at least one embodiment the vent is positioned in an opening of a partition wall. The partition wall is constructed of one or more polymer materials that define the vent opening. The vent can be constructed out of a variety of gas permeable materials, and may include materials such as TYVEK®. In some embodiments the vent includes one or more valve mechanisms, (e.g. perforation(s), diaphragm(s), degassing valve(s), etc.) to provide the vent with a one-way direction of potential gas flow.

As indicated above, one of the chambers of the assembly is configured to contain a desiccant. The desiccant can be of any desired configuration and include any known moisture absorber and/or oxygen scavenger. Also as indicated above, one of the chambers is configured to contain a product such as a medical device. Embodiments of the present invention are particularly suited for the long term stable containment of medical devices that employ one or more therapeutic agents (i.e., drug(s), etc.). Examples of such medical devices include drug eluting stents and/or the delivery systems (catheters, etc.) upon which they are mounted.

In some embodiments the assembly is configured to provide a relatively low humidity environment (relative humidity (RH) of about 5 percent or less) for at least one month. In some embodiments the low humidity environment is maintained for at least 18 months.

In addition to providing a unique package assembly having the features described thus far, some embodiments of the present invention are also directed to packaging processes and methods.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
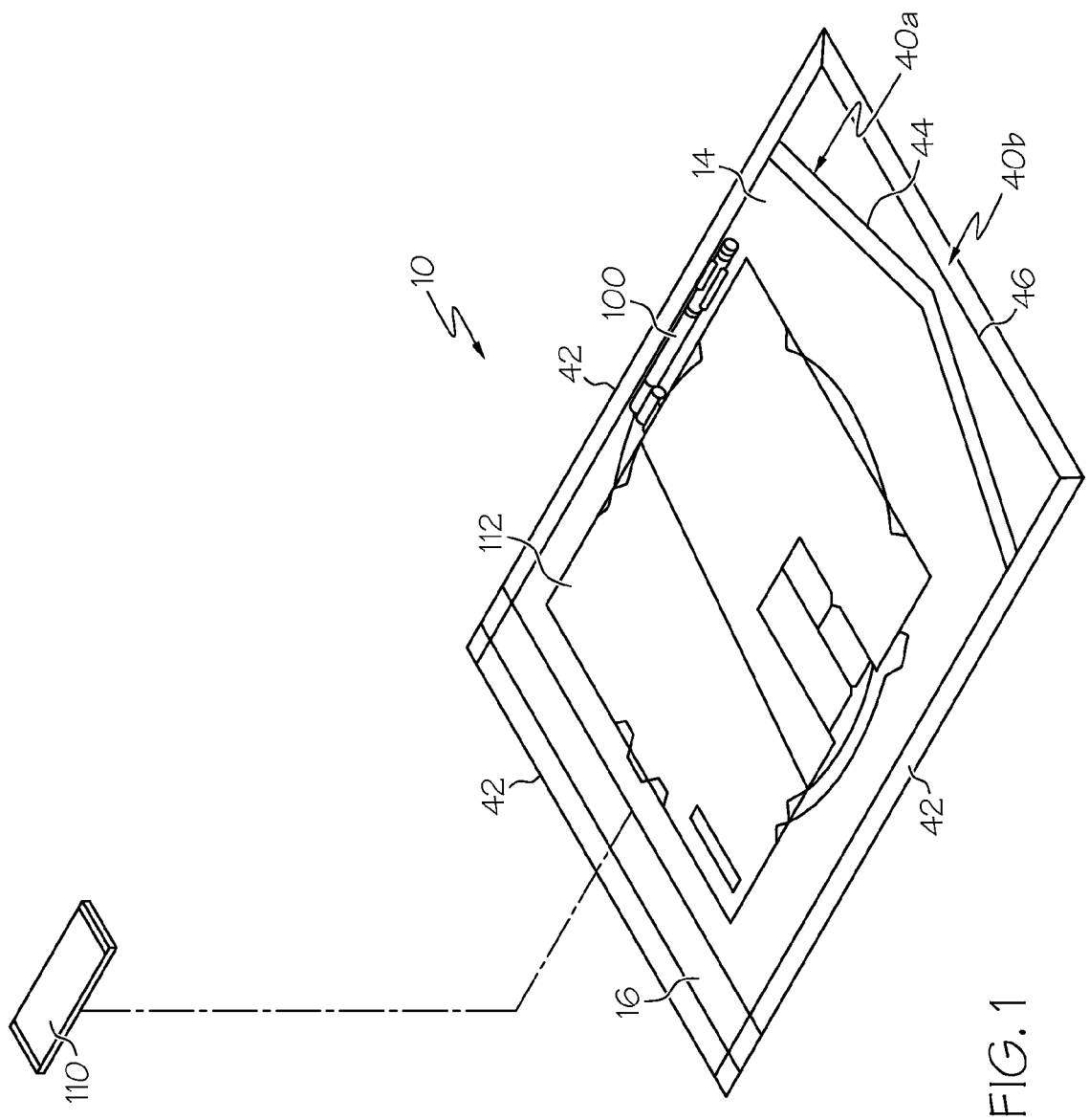
FIG. 1 is a perspective view of an embodiment of the invention including the package assembly with a product contained therein and desiccant depicted externally.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As described above, various embodiments of the present invention are directed to package assemblies. An example of a package assembly 10 is shown in FIG. 1. In some embodiments the assembly 10 is particularly suited for use in the packaging of medical devices, particularly those incorporating a therapeutic agent or drug component. Such medical devices may be of any type, and include implantable medical devices such as stents, and/or the catheters or other delivery systems used to deploy them.

An example of such a medical device product 100 is shown positioned in the interior 12 of a primary chamber 14 of the assembly 10. The interior 12 of assembly 10 also includes a secondary chamber 16, which can be configured to house at least one desiccant 110 (shown externally).

Desiccant 110 can be of any type or configuration known, including but not limited to: silica gel, clay, molecular sieves, potassium permanganate, activated carbon and activated alumina. Examples of oxygen and/or moisture scavengers that may comprise or be incorporated into the desiccant include but are not limited to: calcium oxide, iron oxide powders, sulfites, bisulfites, butylated hydroxytoluene (BHT), butylated hydroxyanisole (BHA), oxygen absorbable polymers, etc.

Figure 2:
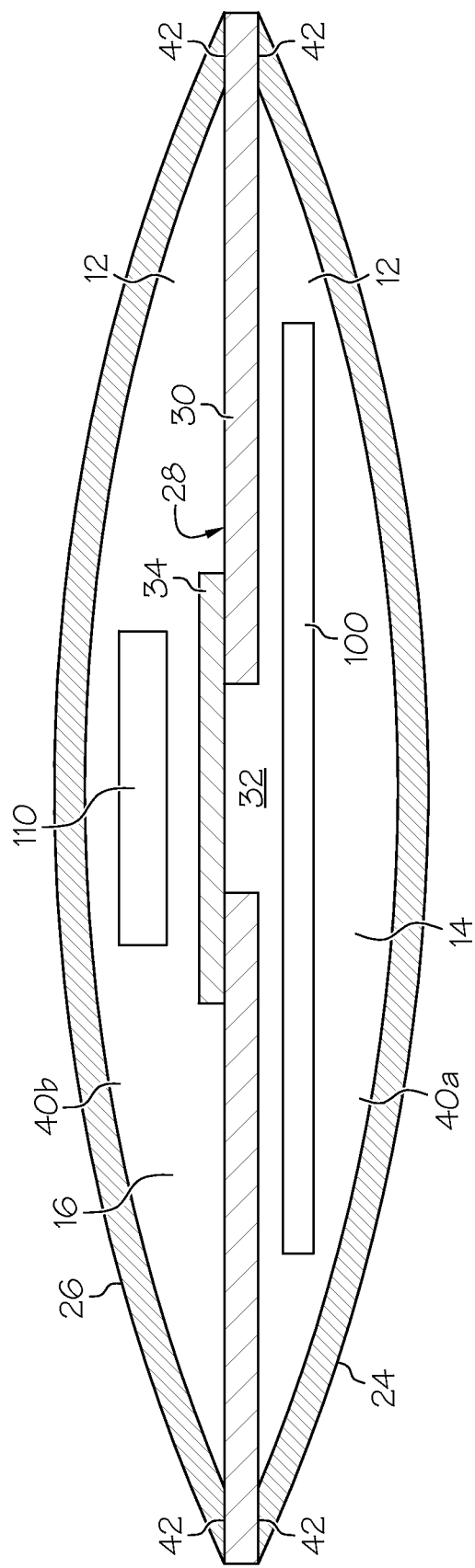
FIG. 2 is a lateral cross-sectional view of the embodiment of FIG. 1.

The division of the package interior 12 into a primary chamber 14 and a secondary chamber 16 is best shown in FIG. 2. As shown, each chamber is defined on its outer perimeter by a wall 24 and 26. Walls 24 and 26 can be of the same materials and/or construction, or distinctly different, depending on a variety of factors that will be discussed in greater detail below. The inner perimeter of each chamber 14 and 16 is defined by a partition 28.

Prior to the closing and sealing of the chambers 14 and 16, each chamber is provided with respective opening 40a and 40b. Openings 40a and 40b can be of any type or mechanism desired. In the embodiment shown in FIGS. 1-2, each of the walls 24 and 26 and partition 28 have corresponding sealed or closed borders 42 that are sealed together during the manufacture of the assembly 10. In the depicted embodiment opening 40a is provided into the primary chamber 14 and defined by the corresponding unsealed or open borders 44 (FIG. 1) of the wall 24 and of the partition 28. Opening 40a is closed by sealing the open borders 44 of wall 24 and partition 28 together. Similarly, opening 40b is provided into the secondary chamber 16 and defined by the corresponding unsealed or open borders 46 (FIG. 1 only) of the wall 26 and of the partition 28. Opening 40b is closed by sealing the open borders 46 of wall 26 and partition 28 together.

The closing and sealing of openings 40a and 40b can be by mechanical engagement, adhesive engagement, by application of a heat seal, etc. In some embodiments opening 40b is capable of being easily and repeatedly being opened and resealed.

Figure 5:
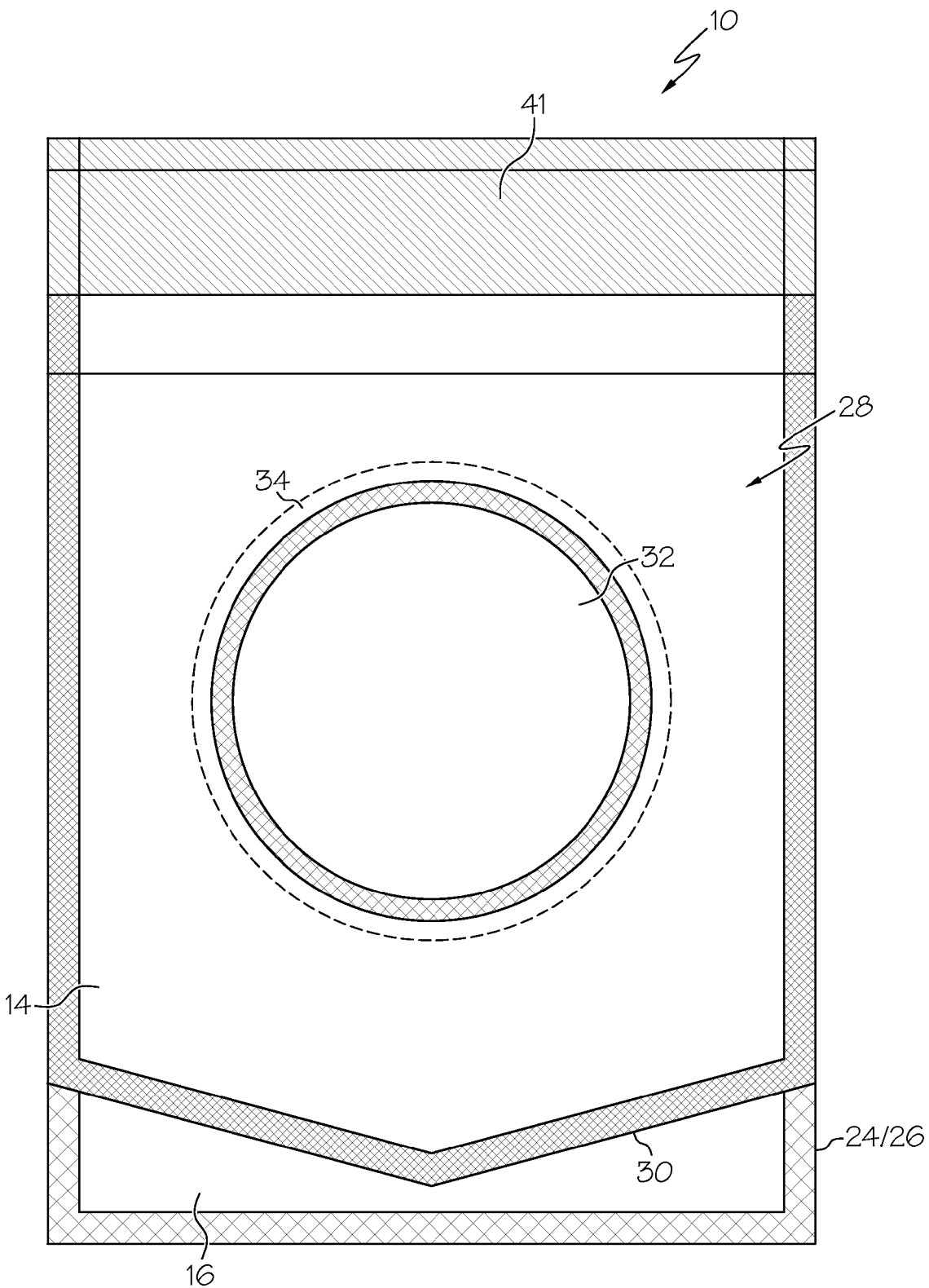
FIG. 5 is a longitudinal cross-sectional view of an embodiment wherein the header region includes a gas permeable header.

In at least one embodiment, an example of which is shown in FIG. 5, the assembly 10 includes a header 41 which includes one or more vented region (see vent 32) similar to that discussed below in regard to the partition 28. The header 41 is a region of the assembly 10 adjacent to the chambers 14 and/or 16. The header 41 can include the region of the assembly defining the openings 40a and/or 40b or be positioned on the opposing end of the assembly 10 such as in the manner shown. The header 41 can be entirely or partially constructed of a gas permeable material such as, for example, TYVEK® thereby allowing increased Ethylene Oxide (EtO) ingress during sterilization of the package assembly 10. Sterilization processes involving the assembly 10 are discussed in greater detail below.

In some embodiments the shape and arrangement of the walls 24 and 26, and the partition 28 can be arranged such that more than one border of a given wall and/or the partition defines the openings 40a and 40b.

Walls 24 and 26 are constructed from at least one layer of polymer material(s), such as for example: polyethylene, which allow the adjacent walls 24 and 26 to be engaged and sealed to one another as well as to the material of the partition 28.

Walls 24 and 26 can be supplemented with a variety of additional material layers (via co-extrusion, lamination, etc.), wherein each layer is selected for desired performance characteristics. For example, embodiments of the invention will include walls 24 and/or 26 having at least one oxygen barrier layer, at least one puncture/tear resistant layer, at least one moisture vapor barrier layer, at least one ultraviolet barrier layer, and any combination thereof.

Some non-limiting examples of materials that provide a desired characteristic are represented as follows:

Oxygen barrier layer: Ethylene-vinyl alcohol copolymer (EVOH), polyvinylidenechloride (PVDC), foil, metallized polyethylene terephthalate (PET)/biaxially oriented nylon (BON), aluminum oxide coatings, silica oxide coatings, polyvinyl alcohol (PVOH), TOPASOR®, and any combinations thereof.

Puncture/Tear resistant layer: BON, bi-axially oriented polypropylene (BOPP), bi-axially oriented polyester (BOPET), linear low-density polyethylene (LLDPE), Ultra Low Density Polyethylene (ULDPE), TYVEK® and any combinations thereof.

Moisture vapor barrier layer: metallized polypropene (PP)/PET/BON, aluminum oxide coated polymers, silica oxide coated polymers, ALCAR®-flourocarbons, and any combinations thereof.

UV barrier layer: foil, metallized PP/PET/BON, polymers with UW blockers.

The particular combination of materials and/or layers of materials in the formation of walls 24 and 26 is tailored to specific packaging requirements of the device to be packaged, the storage environment of the assembly 10, etc. Multiple layers of similar or dissimilar materials, the relative thickness selected for each layer of material, etc., can be modified as desired in order to vary the characteristic properties of the individual materials, the structure of the walls 24 and/or 26, and thus, the performance of the assembly 10 itself.

Figure 3:
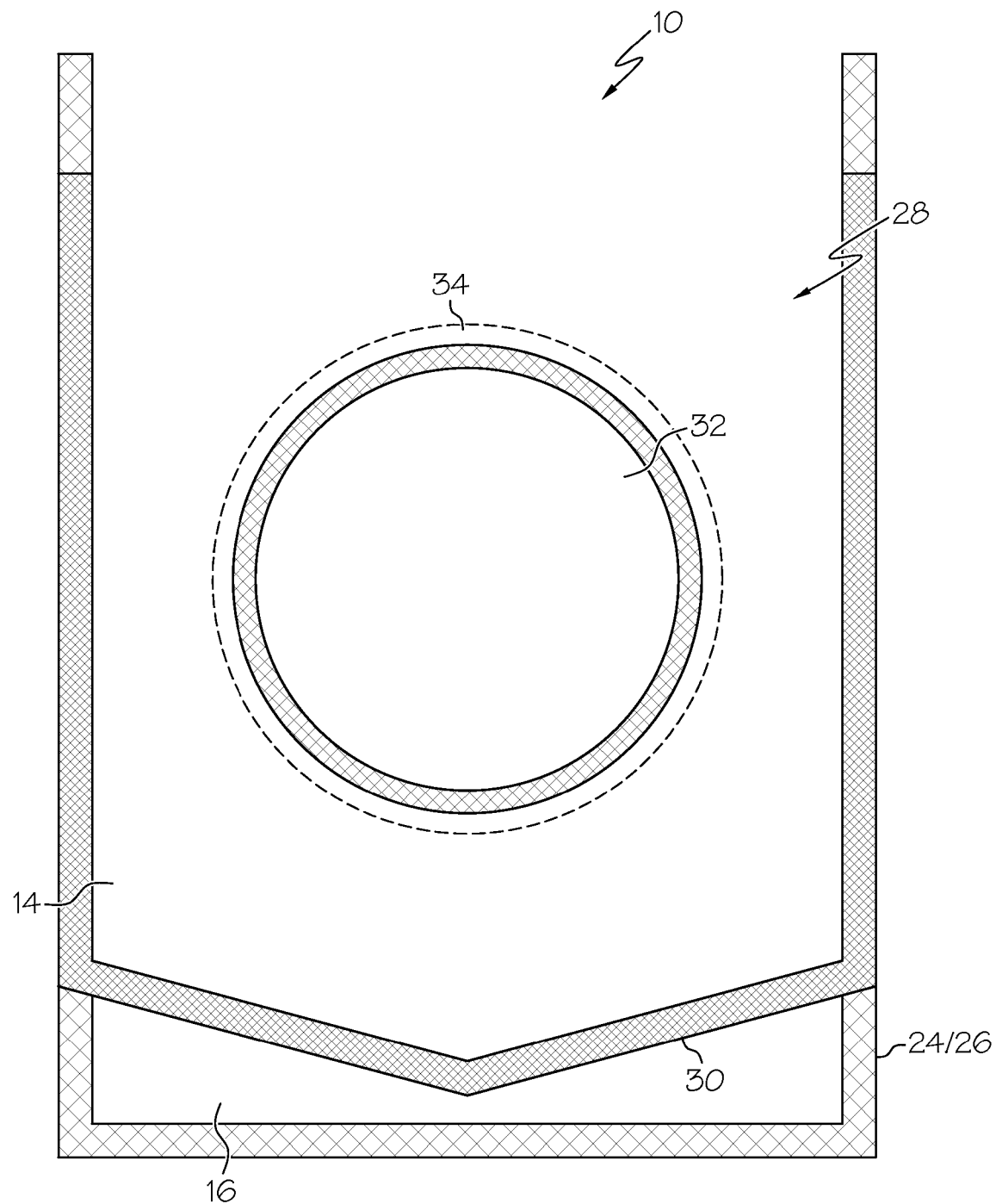
FIG. 3 is a longitudinal cross-sectional view of the embodiment of FIG. 1 wherein the partition structure is illustrated.

In at least one embodiment, the partition 28 comprises at least one sterile, gas permeable or breathable, material(s). In some embodiments, an example of which is shown in FIG. 3 in order to improve the seal between walls 24 and 26 to the partition 28, the partition 28 comprises a housing or housing material 30 that defines an opening 32 therethrough. The housing material 30 may be any type of material selected for flexibility and ease in bonding or sealing with the material of the walls 24 and 26. Some examples of suitable materials include: LLDPE, Nylon, TYVEK®, Foil, etc.

Secured to the housing material 30 across the opening 32 is positioned a vent 34 which is constructed of the previously mentioned gas permeable material(s).

Vent 34 is configured to allow gases to pass from the primary chamber 14 into the secondary chamber 16 both during the packaging process and throughout the shelf-life of the assembly 10. In some embodiments the vent 34 is configured to allow gases as well as moisture to pass in only one direction from the primary chamber 14 and into the secondary chamber 16. While the presence of the desiccant 110, such as is illustrated in FIG. 2, within chamber 16 will facilitate this pathway, vent 34 can also be configured to include a valve, diaphragm or other mechanism to prevent gas or moisture from reentering chamber 14.

Figure 4:
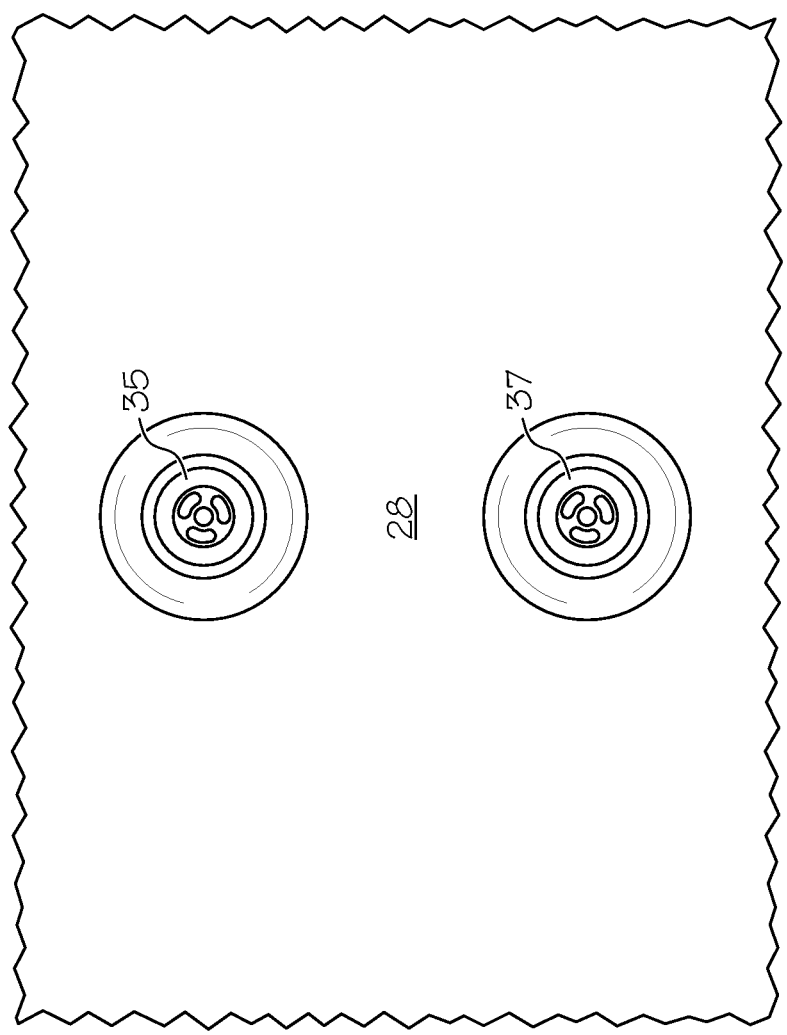
FIG. 4 is a close-up view of an embodiment of the partition shown in FIGS. 2 and 3.

One non limiting example of a degassing valve mechanism suitable for use in partition 38 is described in U.S. Pat. No. 7,178,555 the entire contents of whish is incorporated herein by reference. In at least one embodiment, an example of which is shown in FIG. 4, the partition 28 includes at least one ingress valve 35 and at least one egress valve 37. Another example of a valve mechanism for use in partition 28 includes film and/or tape membranes fabricated on the partition and which overlay pores, slits, holes or other openings through the partition. Other types and configuration of valve mechanisms can alternatively or additionally be incorporated into the partition 28.

In some embodiments the vent has a minimum surface area of about 1 square inch (6.45 cm$^2$). In at least one embodiment the vent has a surface area of at least 9 square inches (58 cm$^2$).

Some examples of sterile, breathable materials that the vent 34 can be constructed from include but are not limited to: medical grade paper, micro-perforated polymer film or films, micro-perforated foil or foils, etc. More specific examples of materials include, but are not limited to: polyethylene, polystyrene, polypropylene, high density polyethylene (HDPE), etc. In at least one embodiment the vent is constructed from a TYVEK®.

With the ability to customize and configure the material composition of the walls 24 and 26, as well as the construction of the partition 28 in mind, an example embodiment of the assembly 10, such as is illustrated in FIG. 2, and which is particularly suited for use with a drug coated medical device is described as follows:

EXAMPLE 1

| Layer Material | Approx. Thickness (mil) |
|---|---|
| Walls 24 and 26 constructed of: | |
| LDPE-EVA (peelable interior) | 2 |
| LDPE | 0.75 |
| BON | 0.60 |
| LDPE | 0.75 |
| Foil | 0.70 |
| White LDPE | 1 |
| PET (exterior) | 0.48 |
| Partition housing material 30 constructed of: | |
| LLDPE | 1.6 |
| Nylon | 0.8 |
| LLDPE | 1.6 |

Vent 34 is constructed of TYVEK ®

In the above example, the various properties that the materials of walls 24 and 26 exhibit, as well as the functional aspect of the partition 28 and desiccant 110; provide a near optimum environment for minimizing potential degradation of a therapeutic coating that a medical device 110 includes. By providing the package assembly interior with total or near total UV protection, optimum moisture protection, and a sterile, sealed environment, the shelf-life of drugs and/or their respective polymer matrices can be maintained for extended periods of time.

Figure 6:
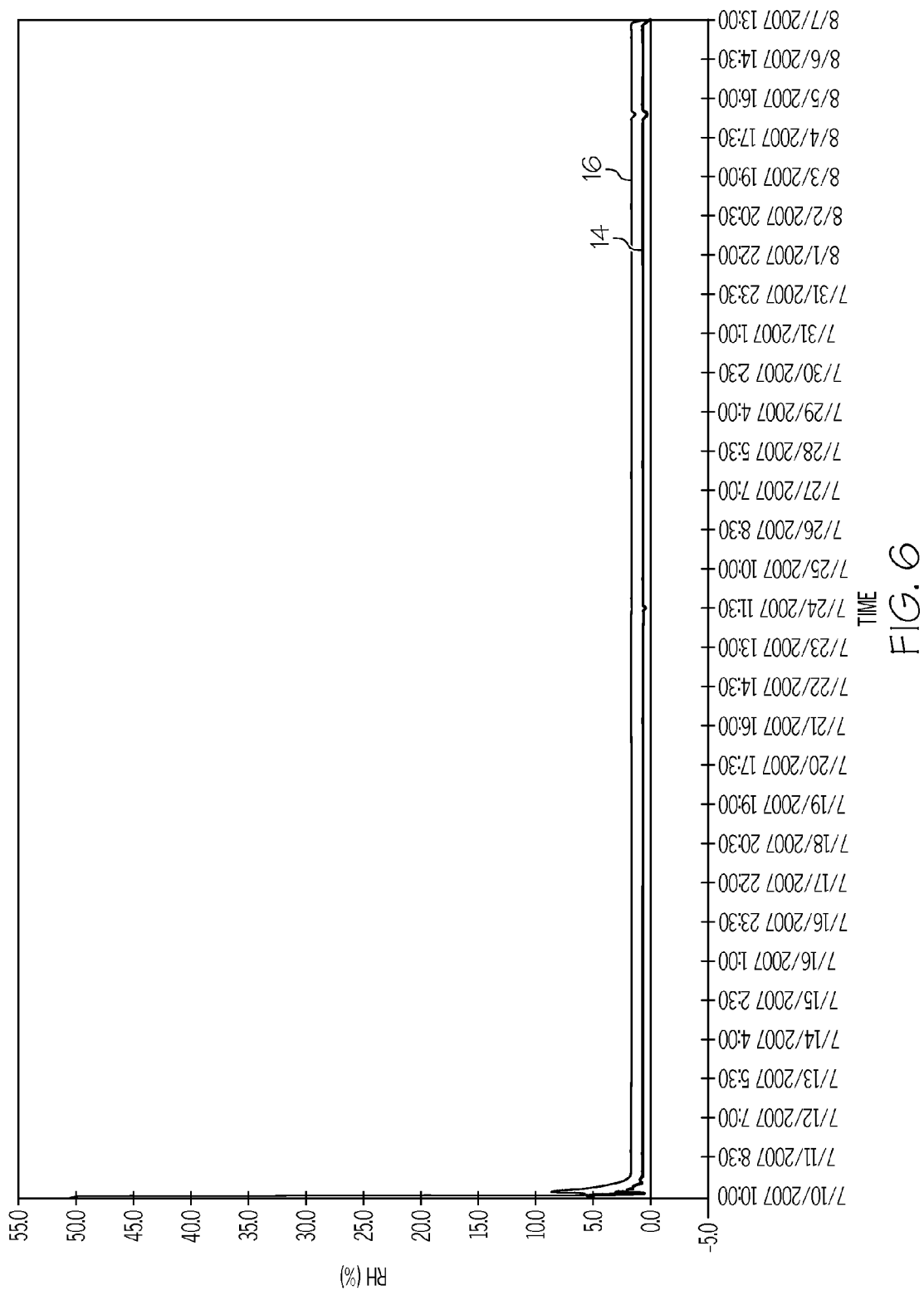
FIG. 6 is a line graph showing the relative humidity of the assembly interior over time.

For example, as illustrated by the chart of FIG. 6, following sterilization and the final sealing of the package assembly, the relative humidity of the primary chamber 14, as well as the secondary chamber 16, is maintained at less than 5% for a duration of at least 1 month. While the example illustrated in FIG. 6 is merely one representative example of the initial performance characteristics of assembly 10 in maintaining a low moisture environment for the short term (about 1 month depicted), in some embodiments similar performance of the assembly 10 is maintained for periods up to and exceeding 18 months.

It should also be noted that FIG. 6 illustrates that shortly after final sealing of the package (approximately 70 hours) the actual relative humidity maintained within the package interior can drop to as low as about 3 percent to about 2 percent over the long term.

Providing a sealed and relatively low humidity environment is a clear benefit to numerous sensitive compositions, such as many of the therapeutic agents utilized with implantable medical devices. Some examples of therapeutic agents that benefit from storage in assembly 10 include but are not limited to the following drugs: Paclitaxel, Evorolimus, Sirolimus, etc. Similarly, polymer matrix materials that are often utilized for the elution of such drugs from a medical device will benefit from the internal environment of assembly 10. Non-limiting examples of such matrix materials include but are not limited to: poly(lactic-co-glycolic acid) (PLGA), Polylactic Acid (PLA), Poly(styrene-b-isobutylene-b-styrene) (SIBS), Poly(dioxanone); poly(trimethylene); poly(caprolactone); polyanhidrides; polyphosphozene; etc.

When used to package an environmentally sensitive product, the insertion of the product into the assembly 10 is but one step in a variety of possible packaging methods or processes.

Figure 7:
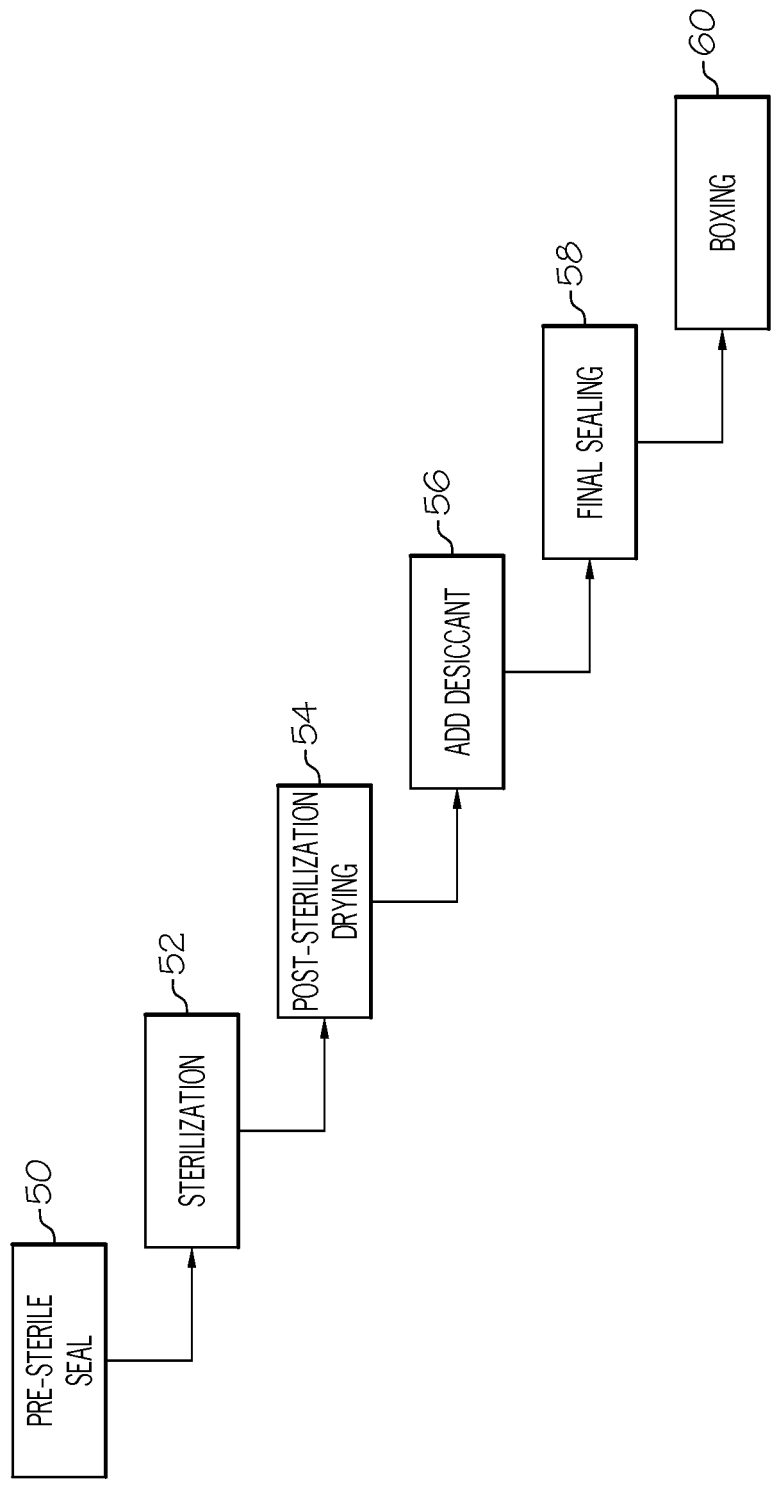
FIG. 7 is a block diagram depicting the steps of a packaging process.

For example, in block diagram depicted in FIG. 7, a process for packaging a medical device is depicted.

Such a process includes the initial step of a pre-sterile seal represented at block 50 wherein the medical device 100 is inserted into the primary chamber 14 of the assembly 10 (shown in FIGS. 1-2) and then the chamber 14 is sealed in the manner previously described. As will be made clear below, step 50 need not be undertaken in a sterile environment, though it can be if desired.

As represented by block 52 once chamber 14 is sealed, secondary chamber 16 remains open and the entire assembly along with the product contained therein is sterilized. The sterilization process may be in accordance with any known sterilization technique, in accordance with the limitations of the product. For example, the assembly can be subjected to e-beam sterilization, Ethylene Oxide (EtO) sterilization, etc.

Depending on the sterilization process utilized, following sterilization the assembly is subjected to vacuum drying as represented by block 54.

As represented by block 56, following the sterilization procedure 52, and optional drying 54, the desiccant 110 is inserted into the secondary chamber 16 (shown in FIGS. 1-2).

Once the desiccant is in position within the secondary chamber the final seal, represented by block 58, is applied to the opening 40b of chamber 16. In some embodiments final seal of the assembly includes the additional steps of applying vacuum to the assembly and/or flushing the assembly interior with an inert gas before the opening of the secondary chamber is sealed.

It is recognized that maintenance of a sterile environment during the entire sealing process is important, particularly where the product in question is an implantable medical device. In some embodiments, the assembly is transferred or kept in a nitrogen cart between the steps of the packaging process described above.

Once the assembly is finally sealed, a label 112 can be applied to the assembly exterior (as depicted in FIG. 1) and the assembly is then boxed for shipment as represented by block 60.

This completes the description of representative embodiments of the invention. Those skilled in the art may recognize other equivalents to the specific embodiment described herein which equivalents are intended to be encompassed by the claims attached hereto.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims.

The invention claimed is:
1. A package assembly comprising:
a first wall and a second wall, the first wall and the second wall comprising at least one layer of at least one gas impermeable material;
a partition being positioned between the first wall and the second wall,
the first wall and a first side of the partition defining a primary chamber, the first wall and the first side each have a plurality of borders engaged to one another, at least one border of the first wall and at least one border of the first side defining an opening to the primary chamber, the at least one border of the of the first wall and the at least one border of the first side being releasably engagable to each other,
the second wall and a second side of the partition defining a secondary chamber, the second wall and the second side each have a plurality of borders engaged to one another, at least one border of the second wall and at least one border of the second side defining an opening to the secondary chamber, the at least one border of the second wall and the at least one border of the second side being releasably engagable to each other,
wherein the partition comprises a vent housing, the vent housing comprises the plurality of borders of the partition, the vent housing defines a vent, and the vent comprises at least one gas permeable material; and
a header region adjacent the primary chamber and the secondary chamber,
wherein the header region comprises a gas permeable material.

2. The assembly of claim 1 wherein at least one of the first wall and the second wall are constructed of a plurality of layers of different materials.

3. The assembly of claim 2 wherein the plurality of layers are selected from the group consisting of: at least one oxygen barrier layer, at least one puncture resistant layer, at least one moisture vapor barrier layer, at least one ultraviolet barrier layer, and any combination thereof.

4. The assembly of claim 2 wherein at least one of the first wall and the second wall comprise at least one layer of a polymer material and at least one layer of foil laminate.

5. The assembly of claim 1 wherein the vent has a surface area of at least 1 square inch.

6. The assembly of claim 1 wherein the vent has a surface area of at least 9 square inches.

7. The assembly of claim 1 wherein the vent is at least partially constructed of high density polyethylene (HDPE).

8. The assembly of claim 1 wherein the vent housing is constructed from at least one layer of polymer material, the vent housing defining an opening therethrough, the vent being engaged to the vent housing and positioned in the opening.

9. The assembly of claim 1 wherein the secondary chamber contains at least one desiccant.

10. The assembly of claim 1 wherein the primary chamber contains a medical device.

11. The assembly of claim 10 wherein the medical device includes a coating of at least one therapeutic agent.

12. The assembly of claim 1 wherein the vent defines a unidirectional gas pathway, wherein gas can pass through the vent only from the primary chamber to the secondary chamber.

* * * * *